United States Patent

Weingarten et al.

(10) Patent No.: US 11,078,146 B2
(45) Date of Patent: Aug. 3, 2021

(54) METHOD FOR PREPARING ETHERS OF CYCLOALIPHATIC OR ARALIPHATIC DIOLS

(71) Applicant: BASF SE, Ludwigshafen am Rhein (DE)

(72) Inventors: Melanie Weingarten, Ludwigshafen am Rhein (DE); Wolfgang Siegel, Ludwigshafen am Rhein (DE); Ralf Pelzer, Lampertheim (DE); Florian Garlichs, Lampertheim (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 16/769,716

(22) PCT Filed: Dec. 3, 2018

(86) PCT No.: PCT/EP2018/083264
§ 371 (c)(1),
(2) Date: Jun. 4, 2020

(87) PCT Pub. No.: WO2019/110464
PCT Pub. Date: Jun. 13, 2019

(65) Prior Publication Data
US 2021/0171427 A1 Jun. 10, 2021

(30) Foreign Application Priority Data

Dec. 4, 2017 (EP) .................................... 17205167

(51) Int. Cl.
C07C 41/06 (2006.01)
C07C 41/01 (2006.01)
C07C 41/05 (2006.01)

(52) U.S. Cl.
CPC ............. C07C 41/06 (2013.01); C07C 41/01 (2013.01); C07C 41/05 (2013.01); C07C 2601/04 (2017.05); C07C 2601/14 (2017.05)

(58) Field of Classification Search
None
See application file for complete search history.

(56) References Cited

U.S. PATENT DOCUMENTS

2013/0252937 A1 9/2013 Eckhardt et al.

FOREIGN PATENT DOCUMENTS

| GB | 1143897 | * | 2/1968 | ............. C07C 31/30 |
| WO | WO-2013004579 A2 | | 1/2013 | |
| WO | WO-2017029312 A1 | | 2/2017 | |

OTHER PUBLICATIONS

International Search Report for PCT/EP2018/083264 dated Mar. 1, 2019.
Naemura, K., et al., "Synthesis and Enantiomer Recognition of Dipodands and Crown Ethers Containing the 2,3:6,7-Dibenzobicyclo[3.3.1]nona-2,6-diene Residue as the Chrial Subunit", Bulletin of the Chemical Society of Japan, vol. 62, No. 1, (1989), pp. 83-88.
Written Opinion of the International Searching Authority for PCT/EP2018/083264 dated Mar. 1, 2019.
Freeman et al., "The Photodecomposition of the Dianion of Tetramethylcyclobutane-1,3-dione Di-p-tosylhydrazone", Journal of Organic Chemistry, vol. 34, No. 6, Jun. 1969, pp. 1751-1759.
International Preliminary Report on Patentability received for PCT Patent Application No. PCT/EP2018/083264, dated Jun. 18, 2020, 7 pages.
Joshi et al., "New Method for the Synthesis of Benzyl Alkyl Ethers Mediated by Fe504", Synthetic Communications, vol. 41, No. 5, 2011, pp. 720-728.
Solladi et al., "A New Class of Chiral Smectic Crystals: Substituted Biphenylylcyclohexylideneethanones Having an Axial Chirality", Journal of Organic Chemistry, vol. 50, No. 21, Jan. 1, 1985, pp. 4062-4068.
US application filed on Mar. 4, 2020, U.S. Appl. No. 16/644,340.

* cited by examiner

Primary Examiner — Rosalynd A Keys
(74) Attorney, Agent, or Firm — Faegre Drinker Biddle & Reath LLP

(57) ABSTRACT

The present invention relates to a method for preparing a dialkyi or dialkenyl ether of a cycloaliphatic or araliphatic diol, which comprises (i) reacting the cycloaliphatic or araliphatic diol with metallic sodium in an aprotic organic solvent in the presence of a catalytic amount of at least one monoether-monoalcohol of formula (I) wherein Y is identical or different and selected from $C_2$-$C_4$-alkylene, n is an integer in the range from 1 to 10, and $R^1$ is $C_1$-$C_4$-Alkyl, whereby the corresponding disodium dialcoholate is obtained, reacting the disodium dialcoholate obtained in step (i) with an alkylation alkenylation reagent.

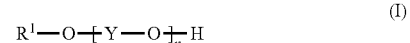

(I)

15 Claims, No Drawings

METHOD FOR PREPARING ETHERS OF CYCLOALIPHATIC OR ARALIPHATIC DIOLS

CROSS-REFERENCE TO RELATED APPLICATIONS

This application is a national stage application (under 35 U.S.C. § 371) of PCT/EP2018/083264, filed Dec. 3, 2018, which claims benefit of European Application No. 17205167.4, filed Dec. 4, 2017, both of which are incorporated herein by reference in their entirety.

The present invention relates to a method for preparing dialkyl or dialkenyl ethers of cycloaliphatic or araliphatic diols.

BACKGROUND OF THE INVENTION

The production of diethers, such as dialkyl or dialkenyl ethers of cycloaliphatic or araliphatic diols, via the direct alkylation of the corresponding diols is challenging, despite the vast number of available synthesis methods. The alkylation of these diols often does not proceed to full completion. As a result, the obtained diether compounds still contain significant amounts of mono-ether species and diol starting material. If harsh reaction conditions are applied in order to drive the reaction to completion and to increase the yield of the diether species, this often also increases the amount of by-products, in particular through elimination reactions. Thus, there is a demand for novel methods that allow the efficient and high yield production of dialkyl or dialkenyl ethers of cycloaliphatic or araliphatic diols via the alkylation of the corresponding diol precursors.

So far, several methods have been described in the art for the preparation of dialkyl or dialkenyl ethers of cycloaliphatic or araliphatic diols.

Solladie et al., Journal of Organic Chemistry, 1985, Vol. 50(21), pp. 4062-4068, describe a method for the production of 1,4-bis(ethoxymethyl)cyclohexane, which comprises the reaction of 1,4-bis(hydroxymethyl)cyclohexane with ethyl iodide in the presence of sodium hydride in tetrahydrofuran. The alkylation reaction is performed under reflux for 16 hours to yield 30% of 4-(ethoxymethyl)-1-(hydroxymethyl)-cyclohexane and 32% of 1,4-bis(ethoxymethyl)cyclohexane.

Freedman et al., J. Org. Chem., 1969, 34, 6, pp. 1751-1759, describe the preparation of the 1,3-dimethoxy-2,2,4,4-tetramethylcyclobutane by reacting 2,2,4,4-tetramethylcyclobutane-1,3-diol with methyl iodide in the presence of sodium hydride in tetrahydrofuran.

WO 2013/004579 describe the preparation of dialkyl- and divinyl-ethers of 1,2-, 1,3- and 1,4-cyclohexanedimethanol by reacting 1,2-, 1,3- and 1,4-cyclohexanedimethanol with an alkyl iodide or with acetylene in the presence of a strong base, such as potassium hydroxide.

WO 2017/029312 describes the preparation of 1,4-bis(ethoxymethyl)cyclohexane by reacting 1,4-bis(hydroxymethyl)cyclohexane with ethyl chloride in the presence of an inorganic base, a solvent and a phase transfer catalyst.

Joshi et al., Synthetic Communications, 2011, Vol. 41, No. 5, pp. 720-728 describe a process for the preparation of 1,4- and 1,2-benzenedimethanol-dialkylethers, respectively, by reacting 1,4- or 1,2-bis(bromomethyl)benzene with the corresponding alkanols in the presence of the Lewis-acid catalyst $FeSO_4$.

The known synthetic methods typically require expensive bases, such as sodium hydride, and/or expensive catalysts. In addition, many of these known synthetic methods suffer from moderate yields, since the alkylation reactions do often not proceed to completion, resulting in the formation of significant amounts of the mono-ether species. If harsh reaction conditions are applied, e.g. reaction conditions used in classical ether synthesis, in order to improve the yield of the di-ether species, the formation of unwanted by-products, which may be difficult to remove from the desired diether compounds, is often increased.

SUMMARY OF THE INVENTION

It is therefore an object of the present invention to provide a method for the production of dialkyl or dialkenyl ethers from cycloaliphatic or araliphatic diols in high yields and selectivities. The method should be simple and efficient. It should allow for mild reaction conditions in order to avoid the formation of unwanted by-products and thus laborious purification procedures. Furthermore, the method should allow for avoiding expensive reagents.

It was surprisingly found, that dialkyl or dialkenyl ethers of cycloaliphatic or araliphatic diols can be obtained in high yields and selectivities by first reacting the cycloaliphatic or araliphatic diols with metallic sodium in the presence of catalytic amounts of a monoether-monoalcohol of the formula (I), as defined herein, to obtain the corresponding disodium dialcoholates, which are then further reacted with an alkylation or alkenylation reagent. The presence of catalytic amounts of a monoether-monoalcohol of the formula (I) in this two-step reaction surprisingly leads to complete alkylation of the cycloaliphatic or araliphatic diols, i.e. the amount of unreacted diol and mono-ether species in the final reaction product is strongly decreased. Furthermore, the presence of catalytic amounts of a monoether-monoalcohol of the formula (I) significantly reduces the exothermic course of the alkylation or alkenylation reaction, which strongly reduces the formation of unwanted side-products.

Therefore, the present invention relates to a method for preparing a dialkyl or dialkenyl ether of a cycloaliphatic or araliphatic diol, which comprises (i) reacting the cycloaliphatic or araliphatic diol with metallic sodium in an aprotic organic solvent in the presence of a catalytic amount of at least one monoether-monoalcohol of formula (I)

wherein
Y is identical or different and selected from $C_2$-$C_4$-alkylene,
n is an integer in the range from 1 to 10, and
$R^1$ is $C_1$-$C_4$-Alkyl,
whereby the corresponding disodium dialcoholate is obtained, (ii) reacting the disodium dialcoholate obtained in step (i) with an alkylation or alkenylation reagent.

Without being bound to theory, it is believed that the presence of catalytic amounts of a monoether-monoalcohol prevents the partial inclusion of the metallic sodium by the disodium salt of the diol starting material (disodium dialcoholate), which immediately forms at the beginning of step (i) of the present invention (deprotonation reaction). Thus, the monoether-monoalcohol keeps the metallic sodium available for further deprotonation reactions leading to the essentially full deprotonation of the diol starting material.

The present process has the following advantages:

The dialkyl or dialkenyl ethers of cycloaliphatic or araliphatic diols can be produced in high yield and selectivity. In particular, the amount of non-alkylated and/or partially alkylated diol in the product mixture is very low.

The dialkyl or dialkenyl ethers of cycloaliphatic or araliphatic diols can be produced without requiring expensive reagents such as sodium hydride or Lewis acid catalysts.

The method of the invention can be performed in a controllable manner, e.g. temperature peaks and/or strong hydrogen gas evolution can be avoided, which makes the reaction safer and reduces the amount of by-products formed.

The work-up and purification of the dialkyl or dialkenyl ethers obtained by the process of the present invention is simple and the desired diethers can be obtained in good purity. Laborious work-up and purification procedures can thus be minimized or avoided.

The method of the invention is simple and efficient. These dialkyl or dialkenyl ethers can therefore be provided without difficulty on industrial scales.

DETAILED DESCRIPTION

In the context of the present invention, the term "alkyl", as used herein, refers to saturated straight-chain or branched hydrocarbon radicals having 1 to 3 ("$C_1$-$C_3$-alkyl"), 1 to 4 ("$C_1$-$C_4$-alkyl") or 1 to 10 ("$C_1$-$C_{10}$-alkyl") carbon atoms. $C_1$-$C_3$-Alkyl is methyl, ethyl, propyl and isopropyl. $C_1$-$C_4$-Alkyl is additionally butyl, 1-methylpropyl (sec-butyl), 2-methylpropyl (isobutyl) or 1,1-dimethylethyl (tert-butyl). $C_1$-$C_{10}$-Alkyl is additionally also, for example, n-pentyl, 1-methylbutyl, 2-methylbutyl, 3-methylbutyl, 2,2-dimethylpropyl, 1-ethylpropyl, 1,1-dimethylpropyl, 1,2-dimethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, or 1-ethyl-2-methylpropyl, n-heptyl, 1-methylhexyl, 2-methylhexyl, 1-ethyl pentyl, 2-ethylpentyl, 1-propylbutyl, 1-ethyl-2-methylbutyl, n-octyl, isooctyl, 2-ethylhexyl, n-nonyl, isononyl, 2-propylhexyl, n-decyl, isodecyl, 2-propylheptyl and the like.

The term "fluoroalkyl" as used herein, refers to straight-chain or branched alkyl groups having 1 to 4 ("$C_1$-$C_4$-fluoroalkyl") carbon atoms (as mentioned above), where some or all of the hydrogen atoms in these groups are replaced by fluorine atoms. Examples for $C_1$-$C_4$-fluoroalkyl are trifluoromethyl, 2,2,2-trifluoroethyl, pentafluoroethyl, 3,3,3-trifluoropropyl, heptafluoropropyl, 1,1,1-trifluoroprop-2-yl, 2,2,2-trifluoro-1-methylethyl, 4,4,4-trifluorobutyl and the like.

The term "alkenyl" as used herein refers to monounsaturated straight-chain or branched hydrocarbon radicals having 2 to 4 ("$C_2$-$C_4$-alkenyl") carbon atoms and a double bond in any position. Examples for $C_2$-$C_4$-alkenyl are ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl or 2-methyl-2-propenyl.

The term "alkylene" as used herein refers to a linear or branched divalent alkanediyl radical having 2 to 4 carbon atoms ("$C_2$-$C_4$-alkylene"). Examples are —$CH_2CH_2$—, —$CH_2CH_2CH_2$—, —$CH(CH_3)CH_2$—, —$CH_2CH(CH_3)$—, —$CH_2CH_2CH_2CH_2$—, —$CH(CH_3)CH_2CH_2$—, —$CH_2CH_2CH(CH_3)$—, —$C(CH_3)_2CH_2$—, —$CH_2C(CH_3)_2$ and positional isomers thereof.

The term "cycloalkylene" as used herein refers to a divalent monocyclic, saturated hydrocarbon group having 3 to 10 ("$C_3$-$C_{10}$-cycloalkylene") carbon atoms as ring members. Examples are cyclopropane-1,2-diyl, cyclobutane-1,2-diyl, cyclobutane-1,3-diyl, cyclopentane-1,2-diyl, cyclopentane-1,3-diyl, cyclohexane-1,2-diyl, cyclohexane-1,3-diyl, cyclohexane-1,4-diyl, cycloheptane-1,2-diyl, cycloheptane-1,3-diyl, cycloheptane-1,4-diyl, cyclooctane-1,2-diyl, cyclooctane-1,3-diyl, cyclooctane-1,4-diyl, cyclooctane-1,5-diyl, cyclononane-1,2-diyl, cyclononane-1,3-diyl, cyclononane-1,4-diyl, cyclononane-1,5-diyl, cyclodecane-1,2-diyl, cyclodecane-1,3-diyl, cyclodecane-1,4-diyl, cyclodecane-1,5-diyl, cyclodecane-1,6-diyl, 1,2,3,3a,4,5,6,6a-octahydropentalene-1,2-diyl, 1,2,3,3a,4,5,6,6a-octahydropentalene-1,3-diyl, 1,2,3,3a,4,5,6,6a-octahydropentalene-1,4-diyl, 1,2,3,3a,4,5,6,6a-octahydropentalene-1,5-diyl, 1,2,3,3a,4,5,6,6a-octahydropentalene-1,6-diyl, 1,2,3,3a,4,5,6,6a-octahydropentalene-2,3-diyl, 1,2,3,3a,4,5,6,6a-octahydropentalene-2,4-diyl, 1,2,3,3a,4,5,6,6a-octahydropentalene-2,5-diyl, 2,3,3a,4,5,6,7,7a-octahydro-1H-indene-1,2-diyl, 2,3,3a,4,5,6,7,7a-octahydro-1H-indene-1,3-diyl, 2,3,3a,4,5,6,7,7a-octahydro-1H-indene-1,4-diyl, 2,3,3a,4,5,6,7,7a-octahydro-1H-indene-1,5-diyl, 2,3,3a,4,5,6,7,7a-octahydro-1H-indene-1,6-diyl, 2,3,3a,4,5,6,7,7a-octahydro-1H-indene-1,7-diyl, 2,3,3a,4,5,6,7,7a-octahydro-1H-indene-2,3-diyl, 2,3,3a,4,5,6,7,7a-octahydro-1H-indene-2,4-diyl, 2,3,3a,4,5,6,7,7a-octahydro-1H-indene-2,5-diyl, 2,3,3a,4,5,6,7,7a-octahydro-1H-indene-2,6-diyl, 2,3,3a,4,5,6,7,7a-octahydro-1H-indene-2,7-diyl, decaline-1,2-diyl, decaline-1,3-diyl, decaline-1,4-diyl, decaline-1,5-diyl, decaline-1,6-diyl, decaline-1,7-diyl, decaline-1,8-diyl, decaline-2,3-diyl, decaline-2,4-diyl, decaline-2,5-diyl, decaline-2,6-diyl, decaline-2,7-diyl, and the like.

"Substituted $C_3$-$C_{10}$-cycloalkylene" refers to a divalent monocyclic or bicyclic, saturated hydrocarbon group having 3 to 10 carbon atoms as ring members, as defined above, substituted by 1, 2, 3, 4 or 5 radicals selected from $C_1$-$C_4$-alkyl, preferably from ethyl and methyl, in particular from methyl.

The term "arylene" as used herein refers to a divalent aromatic substituent containing a single aromatic ring or two aromatic rings, which are fused together or linked covalently, having 6 to 12 ("$C_6$-$C_{12}$-arylene") carbon atoms as ring members. Examples are benzene-1,2-diyl, benzene-1,3-diyl, benzene-1,4-diyl, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,4-diyl, naphthalene-2,5-diyl, naphthalene-2,6-diyl, naphthalene-2,7-diyl, [1,1'-biphenyl]-2,2'-diyl, [1,1'-biphenyl]-2,3'-diyl, [1,1'-biphenyl]-2,4'-diyl, [1,1'-biphenyl]-3,3'-diyl, [1,1'-biphenyl]-3,4'-diyl, [1,1'-biphenyl]-4,4'-diyl and the like.

The term "substituted $C_6$-$C_{12}$-arylene" as used herein refers to a divalent aromatic substituent containing a single aromatic ring or two aromatic rings, which are fused together or linked covalently, as defined above, and which are substituted by 1, 2, 3, 4 or 5 radicals selected from $C_1$-$C_4$-alkyl, preferably from ethyl and methyl, in particular from methyl. Examples are 3-methyl-benzene-1,2-diyl, 4-methyl-benzene-1,2-diyl, 3,4-dimethyl-benzene-1,2-diyl, 3,5-dimethyl-benzene-1,2-diyl, 3,6-dimethyl-benzene-1,2-diyl, 4,5-dimethyl-benzene-1,2-diyl, 3,4,5,6-tetramethyl-benzene-1,2-diyl, 2-methyl-benzene-1,3-diyl, 4-methylbenzene-1,3-diyl, 5-methyl-benzene-1,3-diyl, 2,4-dimethyl-benzene-1,3-diyl, 2,5-dimethyl-benzene-1,3-diyl, 4,5-dimethyl-benzene-1,3-diyl, 4,6-dimethyl-benzene-1,3-diyl, 2,4,5,6-tetramethyl-benzene-1,3-diyl, 2-methyl-benzene-1,4-diyl, 2,3-dimethyl-benzene-1,4-diyl, 2,5-dimethyl-benzene-1,4-diyl, 2,6-dimethyl-benzene-1,4-diyl, 4,5-dimethyl-benzene-1,2-diyl, 2,3,5,6-tetramethyl-benzene-1,4-diyl, and the like.

Step (i):

In step (i) of the method of the present invention, a cycloaliphatic or araliphatic diol is reacted with metallic sodium in an aprotic organic solvent in the presence of a catalytic amount of at least one monoether-monoalcohol of formula (I), as described herein, whereby the corresponding disodium dialcoholate is obtained.

Generally, any monoether-monoalcohol of formula (I) is effective as catalyst and can thus be used in the method of the present invention.

With regard to formula (I), the variables Y, n and $R^1$, alone or in combination, preferably have the following meanings
Y is identical or different and selected from $C_2$-$C_3$-alkylene, in particular from 1,2-ethanediyl, 1,2-propanediyl and 1,3-propanediyl;
n is an integer in the range from 1 to 5, in particular in the range from 1 to 3;
$R^1$ is $C_1$-$C_4$-alkyl, in particular methyl or ethyl.

In particular, the monoether-monoalcohol of formula (I) is selected from compounds, where
Y is identical or different and selected from 1,2-ethanediyl, 1,2-propanediyl and 1,3-propanediyl;
n is 1, 2 or 3;
$R^1$ is methyl or ethyl.

More preferably, the at least one monoether-monoalcohol used in the method of the present invention is selected from the group consisting of
2-methoxyethanol, 2-ethoxyethanol, 3-methoxy-1-propanol, 3-ethoxy-1-propanol, 1-methoxy-2-propanol, 1-ethoxy-2-propanol, 2-methoxy-1-propanol, 2-ethoxy-1-propanol, 2-(2-methoxyethoxy)ethanol, 2-(2-ethoxyethoxy)ethanol, 3-(3-methoxy-1-propoxy)-1-propanol, 3-(3-ethoxy-1-propoxy)-1-propanol, 1-(2-methoxy-1-methylethoxy)-2-propanol, 1-(2-ethoxy-1-methylethoxy)-2-propanol, 1-(2-methoxypropoxy)-2-propanol, 1-(2-ethoxypropoxy)-2-propanol, 2-(2-methoxypropoxy)-1-propanol, 2-(2-ethoxypropoxy)-1-propanol, 2-(2-methoxy-1-methylethoxy)-1-propanol, 2-(2-ethoxy-1-methylethoxy)-1-propanol, 2-[2-(2-methoxyethoxy)ethoxy]-ethanol, 2-[2-(2-ethoxyethoxy)ethoxy]-ethanol, 3-[3-(3-methoxypropoxy)propoxy]-propan-1-ol, 3-[3-(3-ethoxypropoxy)propoxy]propan-1-ol, 2-[2-(2-methoxypropoxy)propoxy]-1-propanol, 2-[2-(2-ethoxypropoxy)propoxy]-1-propanol, and mixtures thereof.

In particular, the at least one monoether-monoalcohol is selected from the group consisting of
2-methoxyethanol, 3-methoxy-1-propanol, 1-methoxy-2-propanol, 2-methoxy-1-propanol, 2-(2-methoxyethoxy)ethanol, 3-(3-methoxy-1-propoxy)-1-propanol, 1-(2-methoxy-1-methylethoxy)-2-propanol, 1-(2-methoxypropoxy)-2-propanol, 2-(2-methoxypropoxy)-1-propanol, 2-(2-methoxy-1-methylethoxy)-1-propanol, 2-[2-(2-methoxyethoxy)ethoxy]-ethanol, 3-[3-(3-methoxypropoxy)propoxy]-propan-1-ol, 2-[2-(2-methoxypropoxy)propoxy]-1-propanol, and mixtures thereof.

Typically, the at least one monoether-monoalcohol (I) is applied in step (i) in catalytic amounts, i.e. in amounts of less than 50 mol-%, e.g. in an amount of from 0.5 to 25 mol-%, based on the amount of the cycloaliphatic or araliphatic diol in the reaction mixture.

Preferably, the total amount of the at least one monoether-monoalcohol (I) applied in step (i) is in the range of 1 to 10 mol-%, in particular in the range of from 2 to 8 mol-%, based on the amount of the cycloaliphatic or araliphatic diol in the reaction mixture. By using the method of the present invention, dialkyl or dialkenyl ethers of a multitude of structurally related cycloaliphatic or araliphatic diols as well as of a multitude of structurally unrelated cycloaliphatic or araliphatic diols can be prepared. Thus, the structure of the cycloaliphatic or araliphatic diol applied in the method of the present invention is not of particular importance. Typical, all common cycloaliphatic or araliphatic diols known to the skilled person can be applied in the method of the present invention.

Preferably, the cycloaliphatic or araliphatic diol reacted in the method of the present invention is selected from a compound of the formula (III)

$$HO-L^1-A-L^2-OH \qquad (III)$$

wherein
A is selected from the group consisting of $C_5$-$C_{10}$-cycloalkylene and $C_6$-$C_{12}$-arylene, wherein $C_5$-$C_{10}$-cycloalkylene and $C_6$-$C_{12}$-arylene are, independently of each other, unsubstituted or substituted by 1, 2, 3, 4 or 5 radicals selected from $C_1$-$C_4$-alkyl, and
$L^1$ and $L^2$, independently of one another, are selected from the group consisting of a chemical bond and $C_1$-$C_3$-alkylene, where $C_1$-$C_3$-alkylene is unsubstituted or substituted by 1 or 2 radicals selected from $C_1$-$C_4$-alkyl and cyclopropyl.

More preferably, the cycloaliphatic or araliphatic diol is selected from a compound of formula (III), where L and $L^2$ are identical.

Even more preferably, the cycloaliphatic or araliphatic diol is selected from a compound of formula (III), where L and $L^2$ are identical and selected from a chemical bond and methylene.

It is further preferred that the radical A in the compound of formula (III) is selected from the group consisting of $C_4$-$C_6$-cycloalkylene, which is unsubstituted or substituted by 1, 2, 3 or 4 radicals selected from methyl and ethyl, and 06-arylene, which is unsubstituted or substituted by 1 or 2 radicals selected from methyl and ethyl.

The aforesaid preferred embodiments can be combined with one another as desired.

Examples of preferred diols are cyclobutane-1,2-diol, cyclobutane-1,3-diol, cyclopentane-1,2-diol, cyclopentane-1,3-diol, cyclohexane-1,2-diol, cyclohexane-1,3-diol, cyclohexane-1,4-diol, 1-methyl-cyclobutane-1,2-diol, 3-methyl-cyclobutane-1,2-diol, 1-methyl-cyclopentane-1,2-diol, 3-methyl-cyclopentane-1,2-diol, 4-methyl-cyclopentane-1,2-diol, 2-methyl-cyclopentane-1,3-diol, 4-methyl-cyclopentane-1,3-diol, 3,3-dimethyl-cyclobutane-1,2-diol, 3,4-dimethyl-cyclobutane-1,2-diol, 2,2-dimethyl-cyclobutane-1,3-diol, 2,4-dimethyl-cyclobutane-1,3-diol, 1-methyl-cyclohexane-1,2-diol, 3-methyl-cyclohexane-1,2-diol, 4-methyl-cyclohexane-1,2-diol, 1-methyl-cyclohexane-1,3-diol, 2-methyl-cyclohexane-1,2-diol, 4-methyl-cyclohexane-1,2-diol, 5-methyl-cyclohexane-1,2-diol, 1-methyl-cyclohexane-1,4-diol, 2-methyl-cyclohexane-1,2-diol, 3-methyl-cyclohexane-1,2-diol, 3,4-dimethyl-cyclopentane-1,2-diol, 3,5-dimethyl-cyclopentane-1,2-diol, 4,4-dimethyl-cyclopentane-1,2-diol, 2,4-dimethyl-cyclopentane-1,3-diol, 4,5-dimethyl-cyclopentane-1,3-diol, 2,2-dimethyl-cyclopentane-1,3-diol, 4,4-dimethyl-cyclopentane-1,3-diol, 3,3,4-trimethyl-cyclobutane-1,2-diol, 2,2,4-trimethyl-cyclobutane-1,3-diol, 3,4-dimethyl-cyclohexane-1,2-diol, 3,5-dimethyl-cyclohexane-1,2-diol, 4,5-dimethyl-cyclohexane-1,2-diol, 2,4-dimethyl-cyclohexane-1,3-diol, 2,5-dimethyl-cyclohexane-1,3-diol, 4,5-dimethyl-cyclohexane-1,3-diol, 2,3-dimethyl-cyclohexane-1,4-diol, 2,5-dimethyl-cyclohexane-1,4-diol, 3,5-dimethyl-cyclohexane-1,4-diol, 3,4,5-trimethylcyclopentane-1,2-diol, 3,3,4-trimethylcyclopentane-1,2-diol, 3,3,5-trimethylcyclopentane-1,2-diol, 3,4,4-trimethylcyclopentane-1,2-diol, 2,4,5-trimethylcyclopentane-1,3-diol, 2,2,4-trimethylcyclopentane-1,3-diol, 4,4,5-trimethylcyclopentane-1,3-diol, 2,4,4-trimethylcyclopentane-1,3-diol, 3,3,4,4-tetramethyl-cyclobutane-1,2-diol, 2,2,4,4-tetramethyl-cyclobutane-1,3-diol, 3,4,5-trimethyl-cyclohexane-1,2-diol, 3,4,6-trimethyl-cyclohexane-1,2-diol, 2,4,5-trimethyl-cyclohexane-1,3-diol, 2,4,6-trimethyl-cyclohexane-1,3-diol, 4,5,6-trimethyl-cyclohexane-1,3-diol, 2,3,5-trimethyl-cyclohexane-1,4-diol, 2,3,6-trimethyl-cyclohexane-1,4-diol, 3,3,4,5-tetramethyl-cyclopentane-1,2-diol, 3,4,4,5-tetramethyl-cyclopentane-1,2-diol, 3,3,4,4-tetramethyl-cyclopentane-1,2-diol, 3,3,5,5-tetramethyl-cyclopentane-1,2-diol, 2,2,4,5-tetramethyl-cyclopentane-1,3-diol, 2,4,4,5-tetramethyl-cyclopentane-1,3-diol, 2,2,4,4-tetramethyl-cyclopentane-1,3-diol, 4,4,5,5-tetramethyl-cyclopentane-1,3-diol, 3,4,5,6-tetramethyl-cyclohexane-1,2-diol, 2,4,5,6-tetramethyl-cyclohexane-1,3-diol, 2,3,5,6-tetramethyl-cyclohexane-1,4-diol, 3,3,4,4,5-pentamethyl-cyclopentane-1,2-diol, 3,3,4,5,5-pentamethyl-cyclopentane-1,2-diol, 2,2,4,4,5-pentamethyl-cyclopentane-1,2-diol, 2,4,4,5,5-pentamethyl-cyclopentane-1,2-diol, benzene-1,2-diol, benzene-1,3-diol, benzene-1,4-diol, 3-methyl-benzene-1,2-diol, 4-methyl-benzene-1,2-diol, 3,4-dimethyl-benzene-1,2-diol, 3,5-dimethyl-benzene-1,2-diol, 3,6-dimethyl-benzene-1,2-diol, 4,5-dimethyl-benzene-1,2-diol, 3,4,5,6-tetramethyl-benzene-1,2-diol, 2-methyl-benzene-1,3-diol, 4-methyl-benzene-1,3-diol, 5-methyl-benzene-1,3-diol, 2,4-dimethyl-benzene-1,3-diol, 2,5-dimethyl-benzene-1,3-diol, 4,5-dimethyl-benzene-1,3-diol, 4,6-dimethyl-benzene-1,3-diol, 2,4,5,6-tetramethyl-benzene-1,3-diol, 2-methyl-benzene-1,4-diol, 2,3-dimethyl-benzene-1,4-diol, 2,5-dimethyl-benzene-1,4-diol, 2,6-dimethyl-benzene-1,4-diol, 4,5-dimethyl-benzene-1,2-diol, 2,3,5,6-tetramethyl-benzene-1,4-diol, and the like.

In particular, the cycloaliphatic or araliphatic diol is selected from a compound of the general formulae (III.a) to (III.g),

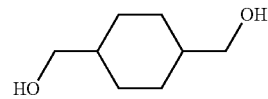

(III.a)

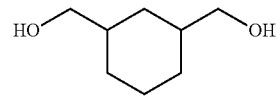

(III.b)

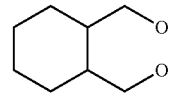

(III.c)

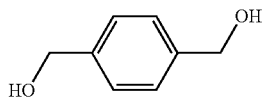

(III.d)

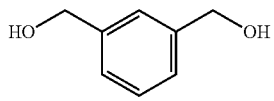

(III.e)

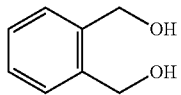

(III.f)

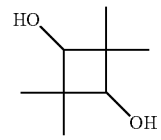

(III.g)

According to the method of the present invention, step (i) is carried out in the presence of an aprotic organic solvent.

In this context, the term "aprotic organic solvent" refers to a solvent that is not capable of exchanging protons with the starting materials, reagents and reaction products present in the reaction mixture.

Suitable aprotic organic solvents include, but are not limited to the following groups:
  group S1: aliphatic and alicyclic hydrocarbons, in particular alkanes and cycloalkanes having 5 to 12 carbon atoms and mixtures of these alkanes and cycloalkanes, such as pentane, hexane, heptane, octane, ligroin, petrol ether or cyclohexane;
  group S2: aromatic hydrocarbons, such as benzene, toluene, xylenes, ethylbenzene or tetralin, and mixtures thereof;
  group S3: aliphatic and alicyclic ethers, such as methyl-tert.-butyl ether, tetrahydrofuran, 1,4-dioxane, alkylene glycol dialkyl ethers, dialkylene glycol dialkyl ethers, polyalkylene glycol dialkyl ethers and mixtures thereof;
as well as mixtures of the aforementioned solvents.

Preferably, the aprotic organic solvent is selected from aliphatic hydrocarbons and solvents of the groups S2 and aliphatic ethers, as well as mixtures thereof.

More preferably, the aprotic organic solvent is selected from solvents of the group S2, alkylene glycol dialkyl ethers, dialkylene glycol dialkyl ethers, polyalkylene glycol dialkyl ethers, as well as mixtures thereof.

In particular, the aprotic organic solvent is selected from benzene, toluene, xylenes, ethylbenzene, 1,2-dimethoxyethyl, 1,2-dimethoxypropyl, 1,3-dimethoxypropyl, 1-methoxy-2-(2-methoxyethoxy)ethane, 1-methoxy-2-(2-methoxypropoxy)propane, 2-methoxy-1-(2-methoxypropoxy)propane, 1-methoxy-3-(3-methoxypropoxy)propane, 1-methoxy-2-[2-(2-methoxyethoxy)ethoxy]ethane, 1-methoxy-2-[2-(2-methoxypropoxy)-propoxy]propane, 2-methoxy-1-[2-(2-methoxypropoxy)propoxy]propane, 1-methoxy-2-[2-(2-methoxypropoxy)-1-methyl-ethoxy]propane, 1,2-diethoxyethyl, 1,2-diethoxypropyl, 1,3-diethoxypropyl, 1-ethoxy-2-(2-ethoxyethoxy)ethane, 1-ethoxy-2-(2-ethoxy-propoxy)propane, 2-ethoxy-1-(2-ethoxypropoxy) propane, 1-ethoxy-3-(3-ethoxy-propoxy)propane, 1-ethoxy-2-[2-(2-ethoxyethoxy)ethoxy]ethane, 1-ethoxy-2-[2-(2-ethoxypropoxy)-propoxy]propane, 2-ethoxy-1-[2-(2- ethoxypropoxy)propoxy]propane, 1-ethoxy-2-[2-(2-ethoxypropoxy)-1-methylethoxy]propane, as well as mixtures thereof.

Especially, the aprotic organic solvent is selected from toluene, xylenes, 1,2-dimethoxyethyl, 1,2-dimethoxypropyl, 1,3-dimethoxypropyl, 1-methoxy-2-(2-methoxyethoxy)ethane, 1-methoxy-2-(2-methoxypropoxy)propane, 2-methoxy-1-(2-methoxypropoxy)propane, 1-methoxy-3-(3-methoxypropoxy)propane, 1-methoxy-2-[2-(2-methoxyethoxy)ethoxy]ethane, as well as mixtures thereof.

According to step (i) of the method of the present invention, the cycloaliphatic or araliphatic diol, as defined above, is reacted with metallic sodium.

Typically, the amount of metallic sodium applied in step (i) is chosen such that the diol in the reaction mixture can be fully transferred into the corresponding disodium dialcoholate.

Preferably, the molar ratio of metallic sodium to cycloaliphatic or araliphatic diol applied in step (i) of the present process is in the range of from 1.8:1 to 4:1, more preferably in the range of from 1.9:1 to 3:1, in particular in the range of from 1.95:1 to 2.5:1.

Step (i) of the present method can be performed in the absence of or in the presence of an inert gas. The expression "inert gas" generally means a gas, which under the prevailing reaction conditions does not enter into any reactions with the starting materials, reagents, or solvents participating in the reaction, or with the resultant products. Examples of inert gases are $N_2$, $CO_2$ and noble gases like He, Ne, Ar, Kr and Xe. It is preferable that step (i) takes place without addition of any inert gas.

Step (i) of the present method can be performed at atmospheric pressure or at elevated pressure. If the reaction is performed at elevated pressure, the pressure is typically in the range of 1.1 to 50 bar, preferably in the range of 1.5 to 30 bar, in particular in the range of 2 to 20 bar. Preferably, the process of the present invention is performed at atmospheric pressure.

Step (i) of the present method is typically carried out at a temperature in the range of from 50 to 250° C., preferably in the range of from 60 to 200° C., in particular in the range of 70 to 180° C.

In a first preferred embodiment of the present invention, step (i) of the present method is conducted such that first the metallic sodium is emulsified in the inert organic solvent comprising a catalytic amount of the monoether-monoalcohol of formula (I) followed by the addition of the cycloaliphatic or araliphatic diol to the emulsified metallic sodium.

The metallic sodium is emulsified in the inert organic solvent under vigorous stirring. Typically, the metallic sodium is emulsified in the inert organic solvent at a temperature, which is equal or above the melting temperature of metallic sodium. Preferably, the metallic sodium is emulsified in the inert organic solvent at a temperature in the range of from 98 to 200° C., more preferably in the range of from 100 to 180° C., in particular in the range of from 100 to 150° C.

Generally, the cycloaliphatic or araliphatic diol is added to the metallic sodium, which is emulsified in the inert organic solvent comprising a catalytic amount of the monoether-monoalcohol of the formula (I), such that the hydrogen evolution can be controlled, i.e. the hydrogen evolution does not exaggerate. Accordingly, the cycloaliphatic or araliphatic diol is preferably added to the emulsified metallic sodium over a period of from 5 minutes to 5 hours, more preferably over a period of from 10 minutes to 2 hours. The cycloaliphatic or araliphatic diol is preferably added to the emulsified metallic sodium, in 3 to 50 portions or continuously.

In a second preferred embodiment of the present invention, step (i) of the present method is conducted such that first the cycloaliphatic or araliphatic diol is emulsified in the inert organic solvent comprising a catalytic amount of the monoether-monoalcohol of formula (I) followed by the addition of the metallic sodium to the emulsified cycloaliphatic or araliphatic diol.

The cycloaliphatic or araliphatic diol is emulsified in the inert organic solvent under vigorous stirring and typically at elevated temperature. Preferably, the cycloaliphatic or araliphatic diol is emulsified in the inert organic solvent at a temperature in the range of from 30 to 200° C., more preferably in the range of from 40 to 180° C., in particular in the range of from 50 to 150° C.

Generally, the metallic sodium is added to the cycloaliphatic or araliphatic diol, which is emulsified in the inert organic solvent comprising a catalytic amount of the monoether-monoalcohol of the formula (I), such that the hydrogen evolution can be controlled, i.e. the hydrogen evolution does not exaggerate. Accordingly, metallic sodium is preferably added to the emulsified cycloaliphatic or araliphatic diol over a period of from 5 minutes to 5 hours, more preferably over a period of from 10 minutes to 2 hours. The metallic sodium is preferably added to the emulsified cycloaliphatic or araliphatic diol in several portions, e.g. in 3 to 50 portions.

Typically, the metallic sodium is added to the cycloaliphatic or araliphatic diol, which is emulsified in the inert organic solvent comprising a catalytic amount of the monoether-monoalcohol of the formula (I), at a temperature, which is equal or above the melting temperature of metallic sodium. Preferably, the metallic sodium is added to the emulsified cycloaliphatic or araliphatic diol at a temperature in the range of from 98 to 200° C., more preferably in the range of from 100 to 180° C., in particular in the range of from 100 to 150° C.

After complete addition of the metallic sodium to the cycloaliphatic or araliphatic diol or after the complete addition of the cycloaliphatic or araliphatic diol to the metallic sodium, respectively, the reaction mixture is preferably stirred at the above mentioned reaction temperature for an additional 5 minutes to 20 hours.

After completion of the reaction of step (i), the majority, typically at least to 65% by weight, preferably at least to 75% by weight, in particular at least to 90% by weight, of the cycloaliphatic or araliphatic diol in the reaction mixture is present in the form of the corresponding disodium dialcoholate.

Generally, the reaction mixture obtained in step (i) is directly applied to step (ii).

Step (ii):

In step (ii) of the method of the present invention, the disodium dialcoholate obtained in step (i) is reacted with an alkylation or alkenylation reagent.

Generally, any alkylation or alkenylation reagents known to the skilled person and that are commonly used in alkylation or alkenylation reactions can be applied in step (ii) of the present invention.

Preferably, the alkylation or alkenylation reagent is selected from a compound of the formula (II)

wherein
R$^2$ is selected from the group consisting of C$_1$-C$_{10}$-alkyl and C$_2$-C$_4$-alkenyl, and
X represents a leaving group, selected from halogen, such as Cl, Br, I, O—CO—O—R$^2$, O—SO$_2$—O—R$^2$ and O—S(O$_2$)R$^{2a}$, where R$^{2a}$ is selected from the group consisting of phenyl, which is unsubstituted or carries 1, 2 or 3 C$_1$-C$_3$-alkyl radicals, C$_1$-C$_4$-alkyl and C$_1$-C$_4$-fluoroalkyl.
Preferably, the radical R$^2$ in formula (II) is selected from C$_1$-C$_6$-alkyl and C$_2$-C$_3$-alkenyl.

In a preferred embodiment of the present invention, the radical R$^2$ in formula (II) is selected from C$_1$-C$_6$-alkyl, more preferably from C$_1$-C$_3$-alkyl, in particular from ethyl.

If the leaving group is selected from halogen, preference is given to Cl, Br and I, in particular to Cl and Br.

Accordingly, if the leaving group is selected from halogen, preferred alkylation reagents are for example methylchloride, ethylchloride, methylbromide and ethylbromide.

If the leaving group is selected from O—S(O$_2$)R$^{2a}$, preference is given to O—S(O$_2$)R$^{2a}$, where R$^{2a}$ is selected from the group consisting of phenyl, which is unsubstituted or carries 1 methyl radical, methyl, ethyl and trifluoromethyl, in particular O—S(O$_2$)R$^{2a}$ is selected from the group consisting of tosylate, mesylate and triflate.

The aforesaid preferred embodiments can be combined with one another as desired.

Accordingly, in a more preferred embodiment of the present invention, the alkylation or alkenylation reagent applied in step (ii) is selected from a compound of the formula (II) wherein
R$^2$ is selected from the group consisting of C$_1$-C$_6$-alkyl and C$_2$-C$_3$-alkenyl, and
X represents a leaving group, selected from Br and I, O—CO—O—R$^2$, O—SO$_2$—O—R$^2$ and O—S(O$_2$)R$^{2a}$, where R$^{2a}$ is selected from the group consisting of phenyl, which is unsubstituted or carries 1 methyl radicals, methyl, ethyl and trifluoromethyl.

In an even more preferred embodiment of the present invention, the alkylation or alkenylation reagent applied in step (ii) is selected from a compound of the formula (II) wherein
R$^2$ is selected from the group consisting of C$_1$-C$_6$-alkyl and C$_2$-C$_3$-alkenyl, and
X represents a leaving group, selected from O—CO—O—R$^2$ and O—SO$_2$—O—R$^2$.

In an even more preferred embodiment of the present invention, the alkylation or alkenylation reagent applied in step (ii) is selected from a compound of the formula (II) wherein
R$^2$ is selected from the group consisting of C$_1$-C$_6$-alkyl, and
X represents a leaving group, selected from O—CO—O—R$^2$ and O—SO$_2$—O—R$^2$.

In a particularly preferred embodiment of the present invention, the alkylation or alkenylation reagent applied in step (ii) is selected from R$^2$—O—SO$_2$—O—R$^2$, wherein R$^2$ has one of the meanings given above.

In an especially preferred embodiment of the present invention, the alkylation or reagent applied in step (ii) is selected from R$^2$—O—SO$_2$—O—R$^2$, where R$^2$ is selected from C$_1$-C$_3$-alykl, in particular from ethyl.

Typically, step (ii) of the present method is carried out at a temperature in the range of from 50 to 250° C., preferably in the range of from 70 to 200° C., in particular in the range of 80 to 180° C.

Step (ii) of the present method can be performed in the absence of or in the presence of an inert gas, as defined above. It is preferable that step (ii) takes place without addition of any inert gas.

Step (ii) of the present method can be performed at atmospheric pressure or at elevated pressure. If the reaction is performed at elevated pressure, the pressure is typically in the range of 1.1 to 50 bar, preferably in the range of 1.5 to 30 bar, in particular in the range of 2 to 20 bar. Preferably, the process of the present invention is performed at atmospheric pressure.

The addition of the alkylation or alkenylation reagent is conducted such that the heat formation can be controlled, i.e. the reaction temperature can be held constant. Accordingly, the alkylation or alkenylation reagent is preferably added over a period of from 5 minutes to 5 hours, more preferably over a period of from 10 minutes to 2 hours to the disodium dialcoholate obtained in step (i). Preferably, the alkylation or alkenylation reagent is added to the disodium dialcoholate in several portions, e.g. in 3 to 50 portions, or continuously.

After complete addition of the alkylation or alkenylation reagent, the reaction mixture is preferably stirred at the above mentioned reaction temperature for an additional 5 minutes to 10 hours, in particular for an additional 10 minutes to 5 hours.

After completion of the reaction, the resulting reaction mixture is typically subjected to an extractive work-up procedure. For this purpose, water is added to the reaction mixture, which after mixing typically divides into two phases, i. e. a water phase and an organic phase, comprising the desired diether compound, which can be drawn off separately.

In case the phase separation does not occur spontaneously through mechanical sedimentation, an organic solvent, which is not well miscible with water, may be added to the reaction mixture to increase the volume of the organic phase. Additionally or alternatively, the reaction mixture may also be subjected to liquid-liquid extraction processes that are well known to the skilled person.

After removal of the volatile organic components, such as the organic solvent, if present, or the aprotic organic solvent used in steps (i) and (ii), the diether compound can typically be obtained in good purity, e.g. in a purity of at least 70% by weight or at least 80% by weight, while the corresponding mono-ethyl ether typically represents the major side product.

However, if necessary, the purity of the diether compounds obtained by the present method can be further increased by adding an additional purification step. Preferably, the diether compounds obtained by the present method are purified by distillation or by using chromatographic methods, such as column chromatography.

Suitable distillation devices for the purification of the diether compounds obtained by the present method are for example distillation columns, such as tray columns optionally equipped with bubble cap trays, sieve plates, sieve trays, packages or filler materials, or spinning band columns, thin film evaporators, falling film evaporators, forced circulation evaporators, Sambay evaporators, etc. and combinations thereof.

The method according to the present invention can be designed to take place either continuously or batch wise. The batch wise reaction can be conducted in a reaction apparatus conventionally used for reactions performed at elevated pressure, e.g. a stirred reactor, which is optionally equipped with metering devices. If the present method is carried out continuously, the reaction can be performed for example in a tube reactor or in a cascade of two or more stirred reactors, which may be back-mixed or not.

EXAMPLES

The following examples are intended for further illustration of the present invention.

| Abbreviations: | |
| --- | --- |
| GC | Gas Chromatography |
| GC-a % | Gas Chromatography area percent |
| eq | equivalent |
| CHDM | 1,4-cylcohexanedimethanol |
| CHDM-DEE | 1,4-bis(ethoxymethyl)cyclohexane |
| TLC | thin-layer chromatography |
| BDM | 1,4-benzenedimethanol |
| BDM-DEE | 1,4-benzenedimethanol-diethylether |
| BDM-MEE | 1,4-benzenedimethanol-monomethylether |

1. Analytics

The purity of the products was determined by Gas Chromatography area-%:

GC-system: Agilent 6980N;
GC-Column: Agilent DB1701 CB (60 m (Length), 0.25 mm (ID), 0.25 micrometer (film));
Temperature program: 50° C. to 150° C. at 15° C./min, 150° C. to 180° C. at 2° C./min, 180° C. to 300° C. at 15° C./min, 10 min hold.

2. Preparation Examples

For examples 2.1 to 2.4, 1,4-cyclohexanedimethanol was dried at 60° C./50—4 mbar three times with each 100 mL toluene.

2.1 Preparation of 1,4-bis(ethoxymethyl)cyclohexane in the Presence of diethyleneglycolmonomethylether 52.9 g (2.3 eq) of sodium were emulsified in 1009 g=1174 mL of xylenes and 3.6 g=3.5 mL (0.03 eq) of diethyleneglycolmonomethylether at 110° C. and 600 rpm. During 2 h at 110-119° C. 144.2 g (1 eq) of 1,4-cylcohexanedimethanol were added and the reaction mixture was further stirred for 3 h at 110° C. and 600 rpm. A thick white suspension formed. The reaction mixture was further stirred at 110° C. overnight. The suspension turned thicker, but was still stirrable.

208.2 g=176.4 mL (1.35 eq) of diethyl sulfate were then added to the reaction mixture at 130-135° C. and 1000 rpm during 3 h. A slight exotherm was observed and the suspension became thinner. The reaction mixture was stirred for further 4 h at 130° C. and overnight at room temperature at 500 rpm.

Subsequently, 750 mL of dist. water were added to the reaction mixture at room temperature (no exotherm observed). Then the mixture was brought to 80° C. and it was stirred for 2 h (pH=3). Then, phase separation took place at 50° C. for 30 min. 1349 g of organic upper phase containing 14.3 weight-% 1,4-bis(ethoxymethyl)-cyclohexane (CHDM-DEE)=96% yield in a ratio of >380:1 CHDM-DEE:CHDM-monoethylether and a purity of 96 GC-a % and 964 g of aqueous lower phase containing no product via TLC were obtained.

The crude product was purified further by distillation to >99 GC-a % 1,4-bis(ethoxy-methyl)cyclohexane.

2.2 Preparation of 1,4-bis(ethoxymethyl)cyclohexane without diethylene-glycol-monomethylether (Comparative Example)

15.9 g (2.3 eq) of sodium were emulsified in 280 g=322 mL of xylenes at 110° C. and 600 rpm. During 2 h at 110-115° C. 43.3 g (1 eq) of 1,4-cylcohexanedimethanol were added and the reaction mixture was further stirred for 3 h at 110° C. and 600 rpm. A grey suspension formed. A reaction sample (1 drop) quenched with water resulted in gas evolution. The reaction mixture was further stirred at 110° C. overnight. The suspension was still grey and good stirrable.

62.5 g=53 mL (1.35 eq) of diethyl sulfate were then added to the reaction mixture at 130-140° C. during 2.5 h. After ~10% diethyl sulfate addition a strong exotherm was observed (temperature control is reduced to 115° C.), the suspension turned thick and white and gas evolution was observed. After ~30% diethyl sulfate addition exotherm was reduced, the reaction mixture becomes thinner and was stirred for further 4 h at 130° C. and overnight at room temperature at 600 rpm.

Subsequently, 176 mL of dist. water were added to the reaction mixture at room temperature (no exotherm observed) and the mixture was stirred for 2 h. Since no proper phase separation was observed during 30 min, the mixture is brought to 80° C. and it is stirred for 2 h (pH=3). Then, phase separation takes place at 50° C. for 30 min. 324 g of organic upper phase containing 15.2 weight-% 1,4-cyclohexanedimethanol-diethylether (CHDM-DEE)=82% yield in a ratio of 39:1 CHDM-DEE:CHDM-monoethylether and 264 g of aqueous lower phase were obtained.

2.3 Preparation of 1,4-bis(ethoxymethyl)benzene in the Presence of diethylene-glycol-monomethylether 15.9 g (2.3 eq) of sodium and 1.1 g=1.1 mL (0.03 eq) of diethyleneglycolmonomethylether were emulsified in 290 g=337 mL of xylenes at 110° C. and 400 rpm. At 110-114° C. during 2 h, 41.5 g (1 eq) of 1,4-benzenedimethanol were added. The reaction mixture was stirred for further 2 h at 110° C. and 300 rpm. A white suspension formed. A reaction sample (1 drop) quenched with water resulted in gas evolution.

62.5 g=53 mL (1.35 eq) of diethyl sulfate were then added to the reaction mixture at 129-136° C. during 2 h. The reaction mixture behaved slightly exothermic and turns thinner. The mixture was stirred for further 4 h at 130° C. and 300 rpm and overnight at room temperature.

Subsequently, 150 mL of dist. water were added (no exotherm observed) and the mixture was brought to 80° C. and it was stirred for 2 h (pH=3). Then, phase separation took place at 50° C. for 30 min. After phase separation, the aqueous phase was extracted with 50 ml of xylenes.

399 g of organic upper phase and 197 g of aqueous lower phase were obtained. The solvent of the organic phase was removed under reduced pressure (70° C., 5 mbar; 40° C., 0.5 mbar) and resulted in 73.8 g of a liquid showing:
73 GC-a % 1,4-benzenedimethanol-diethylether (BDM-DEE)
17 GC-a % of 1,4-benzenedimethanol-monomethylether (BDM-MEE)
5 GC-a % of 1-(ethoxymethyl)-4-methylbenzene

2.4 Preparation of 1,4-bis(ethoxymethyl)benzene without diethylene-glycol-monomethylether (Comparative Example)

41.5 g (1 eq) of 1,4-benzenedimethanol were emulsified in 280 g=322 mL of ortho-xylenes at 130° C. and 2000 rpm. At 130-135° C. during 1 h 15.9 g (2.3 eq) of sodium were added. The reaction mixture was stirred for further 3 h at 130° C.

A white suspension formed. The reaction mixture was further stirred at 110° C. overnight. A reaction sample (1 drop) quenched with water resulted in gas evolution. 62.5 g=53 mL (1.35 eq) of diethyl sulfate were then added to the reaction mixture at 130-140° C. during 3 h. The reaction mixture behaves exothermic and the suspension becomes jellylike. After ~20% of diethyl sulfate addition the exotherm decreased and the mixture was stirred for further 4 h at 130° C. and overnight at room temperature.

Subsequently, 176 mL of dist. water were added (no exotherm observed) and the mixture was brought to 80° C. and it was stirred for 30 min. Then, phase separation took place at 50° C. for 30 min. 323 g of organic upper phase and 228 g of aqueous lower phase were obtained. The solvent of the organic phase was removed under reduced pressure (70° C., 5 mbar; 40° C., 0.5 mbar) and results 42.24 g of a liquid showing:
59 GC-a % 1,4-benzenedimethanol-diethylether (BDM-DEE)
<1 GC-a % of 1,4-benzenedimethanol-monomethylether (BDM-MEE)
21 GC-a % of 1-(ethoxymethyl)-4-methylbenzene

2.5 Preparation of 2,2,4,4-tetramethyl-1,3-Cyclobutandiol-diethylether in the Presence of diethyleneglycolmonomethylether 2,2,4,4-Tetramethyl-1,3-cyclobutandiol (trans:cis=1:1.46) was dried at 80° C./150—4 mbar three times with toluene resulting in a final water content of 0.2 weight-% (Karl Fischer). 8.98 g (2.3 eq) of sodium were emulsified in 100 g=116 mL of xylenes and 0.61 g=0.59 mL (0.03 eq) of diethyleneglycolmonomethylether at 110° C. and 500 rpm. During 45 min 25 g (1 eq) of 2,2,4,4-tetramethyl-1,3-cyclobutandiol in 50 g of xylenes at 130° C. were added dropwise to the reaction mixture which was at 115-118° C. The reaction mixture was further stirred for 20 h at 115° C. and 250 rpm. A beige suspension formed.

35.4 g=30 mL (1.35 eq) of diethyl sulfate were then added to the reaction mixture at 131-135° C. during 2 h. The reaction mixture was stirred for further 4 h at 130° C. and overnight at room temperature at 250 rpm.

Subsequently, 75 mL of dist. water were added to the reaction mixture at room temperature. Then the mixture is brought to 80° C. and it was stirred for 2 h (pH=3). Then, phase separation takes place at 50° C. for 30 min. The aqueous phase was extracted further two times with 25 mL xylenes each. 212 g of organic upper phase was obtained. GC-analytics showed:
83 GC-a % 2,2,4,4-Tetramethyl-1,3-cyclobutandiol-diethylether (trans:cis=1:3) and
2 GC-a % 2,2,4,4-Tetramethyl-1,3-cyclobutandiolmonoethyl-ether.

2.6 Preparation of 2,2,4,4-tetramethyl-1,3-Cyclobutandiol-diethylether without diethyleneglycolmonomethylether (Comparative Example)

2,2,4,4-Tetramethyl-1,3-cyclobutandiol (trans:cis=1:1.46) was dried at 80° C./150—4 mbar three times with toluene resulting in a final water content of 0.2 weight-% (Karl Fischer). 8.98 g (2.3 eq) of sodium were emulsified in 100 g of xylenes at 110° C. and 500 rpm. During 45 min 25 g (1 eq) of 2,2,4,4-tetramethyl-1,3-cyclobutandiol in 50 g of xylenes at 115° C. were added dropwise to the reaction mixture which is at 115° C. The reaction mixture was further stirred for 18 h at 115° C. and 250 rpm. A white-yellow suspension formed.

35.36 g (1.35 eq) of diethyl sulfate were then added to the reaction mixture at 131-138° C. during 2 h. The white suspension was stirred for further 4 h at 130° C. and overnight at room temperature at 250 rpm.

Subsequently, 50 mL of dist. water are added to the reaction mixture at room temperature. Then the mixture was brought to 80° C. and it was stirred for 2 h (pH=3). Then, phase separation took place at 50° C. for 30 min. The aqueous phase was extracted further two times with 25 mL xylenes each. 220.5 g of organic upper phase was obtained. GC-analytics showed:
1 GC-a % 2,2,4,4-Tetramethyl-1,3-cyclobutandiol,
74 GC-a % 2,2,4,4-Tetramethyl-1,3-Cyclobutandioldiethylether (trans:cis=1:2.4),
11 GC-a % 2,2,4,4-Tetramethyl-1,3-Cyclobutandiolmonoethylether.

The invention claimed is:

1. A method for preparing a dialkyl or dialkenyl ether of a cycloaliphatic or araliphatic diol, which comprises
    (i) reacting the cycloaliphatic or araliphatic diol with metallic sodium in an aprotic organic solvent in the presence of a catalytic amount of at least one monoether-monoalcohol of formula (I)

wherein
Y is identical or different and selected from $C_2$-$C_4$-alkylene,
n is an integer in the range from 1 to 10, and
$R^1$ is $C_1$-$C_4$-alkyl,
whereby the corresponding disodium dialcoholate is obtained,
    (ii) reacting the disodium dialcoholate obtained in step (i) with an alkylation or alkenylation reagent.

2. The method of claim 1, where the amount of the at least one monoether-monoalcohol (I) used in step (i) is in the range of 1 to 10 mol-%, based on the amount of the cycloaliphatic or araliphatic diol.

3. The method of claim 1, where the monoether-monoalcohol of formula (I) is selected from the group consisting of 2-methoxyethanol, 2-ethoxyethanol, 3-methoxy-1-propanol, 3-ethoxy-1-propanol, 1-methoxy-2-propanol, 1-ethoxy-2-propanol, 2-methoxy-1-propanol, 2-ethoxy-1-propanol, 2-(2-methoxyethoxy)ethanol, 2-(2-ethoxyethoxy)ethanol, 3-(3-methoxy-1-propoxy)-1-propanol, 3-(3-ethoxy-1-propoxy)-1-propanol, 1-(2-methoxy-1-methylethoxy)-2-propanol, 1-(2-ethoxy-1-methylethoxy)-2-propanol, 1-(2-methoxypropoxy)-2-propanol, 1-(2-ethoxypropoxy)-2-propanol, 2-(2-methoxypropoxy)-1-propanol, 2-(2-ethoxypropoxy)-1-propanol, 2-(2-methoxy-1-methylethoxy)-1-propanol, 2-(2-ethoxy-1-methylethoxy)-1-propanol, 2-[2-(2-methoxyethoxy)ethoxy]-ethanol, 2-[2-(2-ethoxyethoxy)ethoxy]-ethanol, 3-[3-(3-methoxypropoxy)propoxy]propan-1-ol, 3-[3-(3-ethoxypropoxy)propoxy]propan-1-ol, 2-[2-(2-methoxypropoxy)propoxy]-1-propanol, 2-[2-(2-ethoxypropoxy)propoxy]-1-propanol, and mixtures thereof.

4. The method of claim 1, where the molar ratio of metallic sodium to cycloaliphatic or araliphatic diol is in the range of from 1.8:1 to 4:1.

5. The method of claim 1, where the alkylation or alkenylation reagent is a compound of the formula (II)

$$R^2—X \quad (II)$$

wherein

R² is selected from the group consisting of $C_1$-$C_{10}$-alkyl and $C_2$-$C_4$-alkenyl, and X represents a leaving group, selected from halogen, O—CO—O—R², O—SO₂—O—R² and O—S(O₂)R²ᵃ, where R²ᵃ is selected from the group consisting of phenyl, which is unsubstituted or carries 1, 2 or 3 $C_1$-$C_3$-alkyl radicals, $C_1$-$C_4$-alkyl and $C_1$-$C_4$-fluoroalkyl.

6. The method of claim 5, where in step (ii) R²—O—SO₂—O—R² is used as the alkylation or alkenylation reagent.

7. The method of claim 5, where in formula (II) the radical R² is $C_1$-$C_3$-alkyl.

8. The method of claim 1, where the cycloaliphatic or araliphatic diol is selected from a compound of the formula (III)

$$HO—L^1—A—L^2—OH \quad (III)$$

wherein

A is selected from the group consisting of $C_5$-$C_{10}$-cycloalkylene and $C_6$-$C_{12}$-arylene, wherein $C_5$-$C_{10}$-cycloalkylene and $C_6$-$C_{12}$-arylene are, independently of each other, unsubstituted or substituted by 1, 2, 3, 4 or 5 radicals selected from $C_1$-$C_4$-alkyl, and L¹ and L², independently of one another, are selected from the group consisting of a chemical bond and $C_1$-$C_3$-alkylene, where $C_1$-$C_3$-alkylene is unsubstituded or substituted by 1 or 2 radicals selected from $C_1$-$C_4$-alkyl and cyclopropyl.

9. The method of claim 8, where the compound of formula (III) is selected from one of the following compounds of the general formulae (III.a) to (III.g),

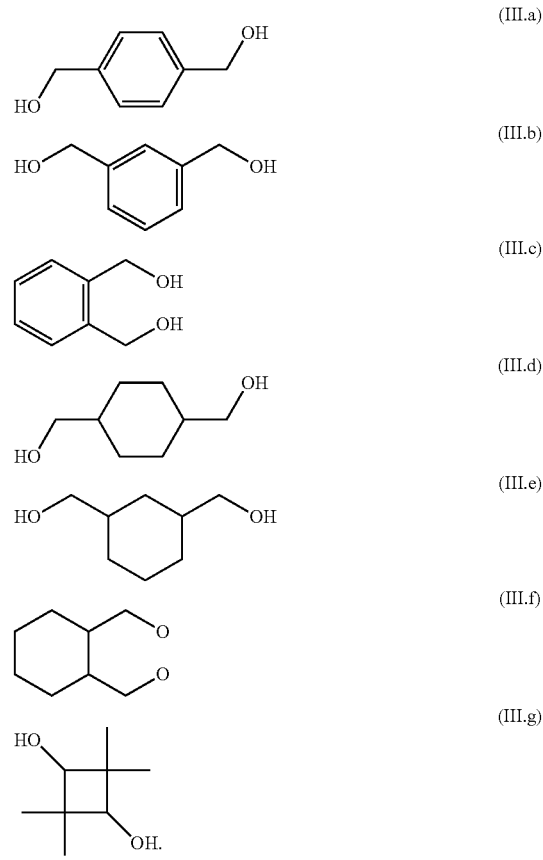

10. The method of claim 1, where in step (i) the metallic sodium is first emulsified in the inert organic solvent comprising a catalytic amount of the monoether-monoalcohol of formula (I) followed by the addition of the cycloaliphatic or araliphatic diol to the emulsified metallic sodium.

11. The method of claim 10, where the cycloaliphatic or araliphatic diol is added to the metallic sodium, which is emulsified in the inert organic solvent comprising a catalytic amount of the monoether-monoalcohol of the formula (I), over a period of from 5 minutes to 5 hours.

12. The method according to claim 1, where in step (i) the cycloaliphatic or araliphatic diol is first emulsified in the inert organic solvent comprising a catalytic amount of the monoether-monoalcohol of formula (I) followed by the addition of the metallic sodium to the emulsified cycloaliphatic or araliphatic diol.

13. The method according to claim 12, where the metallic sodium is added to the cycloaliphatic or araliphatic diol, which is emulsified in the inert organic solvent comprising a catalytic amount of the monoether-monoalcohol (I), over a period of from 5 minutes to 5 hours.

14. The method according to claim 1, where the aprotic organic solvent is selected from aliphatic hydrocarbons, aromatic hydrocarbons, aliphatic ethers and mixtures thereof.

15. The method according to claim 1, where the aprotic organic solvent is selected from aromatic hydrocarbons, alkylene glycol dialkyl ethers, dialkylene glycol dialkyl ethers, polyalkylene glycol dialkyl ethers, and mixtures thereof.

* * * * *